United States Patent [19]
Holderbaum et al.

[11] Patent Number: 6,007,828
[45] Date of Patent: Dec. 28, 1999

[54] COSMETIC PREPARATIONS CONTAINING PHOTOSTABLE UV-A FILTERS

[75] Inventors: Martin Holderbaum, Ludwigshafen; Alexander Aumüller, Neustadt; Karin Sperling, Neustadt; Horst Westenfelder, Neustadt; Thomas Wünsch, Speyer, all of Germany

[73] Assignee: BASF Aktiengesellschaft, Ludwigshafen, Germany

[21] Appl. No.: 09/068,008

[22] PCT Filed: Oct. 25, 1996

[86] PCT No.: PCT/EP96/04637

§ 371 Date: Apr. 29, 1998

§ 102(e) Date: Apr. 29, 1998

[87] PCT Pub. No.: WO97/17054

PCT Pub. Date: May 15, 1997

[30] Foreign Application Priority Data

Nov. 3, 1995 [DE] Germany ............ 195 40 952

[51] Int. Cl.⁶ ............... A61K 7/00; A61K 7/42

[52] U.S. Cl. ............... 424/401; 424/59
[58] Field of Search ................ 424/59, 401

[56] References Cited

U.S. PATENT DOCUMENTS 3,270,045  8/1966  Strobel et al. .......... 260/465
3,275,520  9/1966  Strobel .................. 167/90

FOREIGN PATENT DOCUMENTS 1 309 169  10/1962  France .
1 242 780   7/1960  Germany .
1 221 225   3/1961  Germany .

*Primary Examiner*—Thurman K. Page
*Assistant Examiner*—Sharon Howard
*Attorney, Agent, or Firm*—Keil & Weinkauf

[57] ABSTRACT

A sunscreen-containing cosmetic formulation to protect the human epidermis from UV light in the range from 280 to 400 nm, which formulation includes a cosmetically suitable carrier, together with compounds which absorb in the UV-B region and as photostable UV-A filters effective amounts of compounds of the formula I as defined in the specification.

4 Claims, No Drawings

COSMETIC PREPARATIONS CONTAINING PHOTOSTABLE UV-A FILTERS

DESCRIPTION

The invention relates to the use of substituted diphenylmalononitriles as photostable UV-A filters in cosmetic formulations to protect the human epidermis from UV radiation, specifically in the range from 320 to 400 nm.

The sunscreen agents employed in cosmetic formulations have the task of preventing harmful effects of sunlight on the human skin or at least reducing their consequences. In addition, however, these sunscreen agents also serve to protect other ingredients from decomposition or degradation by UV radiation.

The sunlight reaching the surface of the earth contains UV-B (280 to 320 nm) and UV-A (>320 nm), radiation which is immediately adjacent to the visible light region. The effect on the human skin, especially of UV-B radiation, is manifested by sunburn. Accordingly the industry supplies quite a large number of substances which absorb UV-B radiation and thus prevent sunburn.

Dermatological investigations have now shown that UV-A radiation is also perfectly able to cause skin damage by, for example, damaging the keratin or elastin. This results in a reduction in the elasticity and water-storage capacity of the skin, ie. the skin becomes less supple and is prone to wrinkles. The noticeably high incidence of skin cancer in regions exposed to strong sunlight shows that evidently damage to the genetic information in the cells is also caused by sunlight, specifically by UV-A radiation. All these findings therefore make it appear necessary to develop efficient filter substances for the UV-A region.

There is a growing need for sunscreen agents for cosmetic formulations which can be used in particular as UV-A filters and whose absorption maxima should therefore be in the region from about 320 to 380 nm. In order to achieve the desired effect with use of the minimum amount, sunscreen agents of this type should additionally have a highly specific extinction. In addition, sunscreen agents for cosmetic products must also meet a large number of other requirements, for example good solubility in cosmetic oils, high stability of the emulsions produced with them, toxicological acceptability and little intrinsic odor and color.

Another requirement which must be met by sunscreen agents is adequate photostability. However, this is only inadequately ensured, if at all, with UV-A absorbing sunscreen agents available to date.

French patent No. 2 440 933 describes 4-(1,1-dimethylethyl)-4'-methoxydibenzoylmethane as UV-A filter. The proposal is to combine this specific UV-A filter, which is sold by GIVAUDAN under the name "PARASOL 1789", with various UV-B filters in order to absorb all UV rays with a wavelength from 280 to 380 nm.

However, this UV-A filter has insufficient photochemical stability, when used alone or in combination with UV-B filters, to ensure permanent protection of the skin during lengthy exposure to the sun, which makes repeated applications at regular and short intervals necessary if effective protection of the skin from all the UV rays is desired.

This is why, according to EP 0514491, the UV-A filters with inadequate photostability are to be stabilized by adding 2-cyano-3,3-diphenylacrylic esters which themselves act as filters in the UV-B region.

It is an object of the present invention to propose sunscreen agents for cosmetic purposes which absorb in the UV-A region and are photostable.

We have found that this object is achieved by adding compounds of the formula I

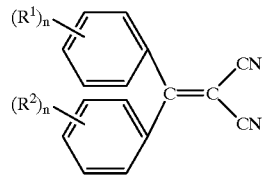

I where $R^1$ and $R^2$ are identical or different straight-chain or branched aliphatic or cycloaliphatic radicals which are in the para and/or ortho position and have 1 to 18 carbon atoms, and where $R^1$ can additionally be a hydrogen atom, and where furthermore n is 1 or 2, when these compounds have their essential absorption in the range from 320 to 380 nm, as UV-A filters in cosmetic formulations to protect the human skin from the sun's rays, together with compounds which absorb in the UV-B region and are known per se for cosmetic formulations.

Aliphatic and cycloaliphatic radicals mean in particular hydrocarbon radicals which may be interrupted by oxygen atoms.

It is preferred in this connection to use compounds of the formula I

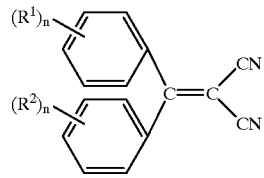

I where $R^1$ and $R^2$ are identical or different and are straight-chain or branched alkyl radicals having 1 to 18 carbon atoms, in which the alkyl chain can be interrupted by oxygen atoms, and where $R^1$ can also be hydrogen, and n is 1 and 2.

Particularly suitable compounds of the formula I are those where $R^1$ and $R^2$ are identical or different branched alkoxy radicals which are in the para position and have 3 to 12 carbon atoms, and n is in each case 1, and $R^1$ can also be hydrogen.

Particularly preferred individual compounds are the following, where $R^1$ and/or $R^2$ are in the para position and are

| | |
|---|---|
| n-propoxy | isopropoxy |
| n-butoxy | 1-methylpropoxy |
| 2-methylpropoxy | n-pentoxy |
| 1,1-dimethylpropoxy | 3-methylbutoxy |
| hexoxy | 2,2-dimethylpropoxy |
| heptoxy | 1-methyl-1-ethylpropoxy |
| 2-ethylhexoxy | and/or octoxy, | and where $R^1$ can also be hydrogen.

The compounds which can be used according to the invention are expediently prepared in a manner known per se by a process disclosed by Georges Charles, Bull.Soc. Chim. 1962, 1559, in which benzophenone is replaced as starting compounds by the corresponding imines of the formula II

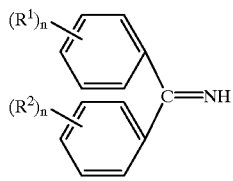

where $R^1$ and $R^2$ and n have the meanings indicated above, with malononitrile in polar organic solvents with exclusion of water.

This process has several advantages: no catalyst is required; the yields are better and the reaction takes place at lower temperatures. The starting compounds of the formula II can be obtained, for example, by the process of DE-A 4442138.

Sunscreen-containing cosmetic formulations are, as a rule, based on a carrier which contains at least one oil phase. However, formulations only with an aqueous (gel) base are also possible. Accordingly, oils, oil-in-water and water-in-oil emulsions, creams and pastes, protective lipstick bases or gels are suitable.

Sunscreen products of these types can accordingly be in liquid, pasty or solid form, for example as water-in-oil creams, oil-in-water creams and lotions, aerosol foam creams, gels, oils, grease pencils, dusting powders, sprays or alcoholic/aqueous solutions.

Examples of conventional oil components in cosmetics are liquid paraffin, glyceryl stearate, isopropyl myristate, diisopropyl adipate, acetylstearyl 2-ethylhexanoate, hydrogenated polyisobutene, petrolatum, caprylic acid/capric acid triglycerides, microcrystalline wax, lanolin and stearic acid.

Examples of conventional cosmetic auxiliaries which may be suitable as additives are emulsifiers such as fatty alcohol ethoxylates, sorbitan fatty acid esters or lanolin derivatives, thickeners such as carboxymethylcellulose or crosslinked polyacrylic acid, preservatives and perfumes. Finally, other substances which absorb in the UV-A region and are known per se can also be used if they are stable in the complete system of the combination of UV-B and UV-A filters to be used according to the invention.

The present invention furthermore relates to cosmetic formulations which comprise 0.1 to 10% by weight, preferably 1 to 7% by weight, based on the total amount of the cosmetic formulation, of one or more of the compounds of the formula I together with compounds which absorb in the UV-B region and are known per se for cosmetic formulations as sunscreen agents, with the compounds of the formula I usually being employed in a smaller amount than the UV-B-absorbing compounds.

Most of the sunscreen agents in the cosmetic formulations used to protect the human epidermis comprise compounds which absorb UV light in the UV-B region, ie. in the range from 280 to 320 nm. Examples of contents of the UV-A absorbers to be used according to the invention are from 10 to 90% by weight, preferably 20 to 50% by weight, based on the total amount of UV-B- and UV-A-absorbing substances.

Any UV-B filter substances are suitable as UV-B filter substances used in combination with the compounds of the formula I to be used according to the invention. Examples which may be mentioned are:

| No. | Substance | CAS No. (=acid) |
|---|---|---|
| 1 | 4-Aminobenzoic acid | 150-13-0 |
| 2 | 3-(4'Trimethylammonium)benzylidenebornan-2-one methyl sulfate | 52793-97-2 |
| 3 | 3,3,5-Trimethylcyclohexyl salicylate (Homosalatum) | 118-56-9 |
| 4 | 2-Hydroxy-4-methoxybenzophenone (Oxybenzonum) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)-bis(7,7-dimethyl-2-oxobicyclo[2.2.1]heptane-1-methanesulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | 2-Isoamyl 4-methoxycinnamate | 7/6/7-10-2 |
| 11 | 2-Ethylhexyl 4-methoxycinnamate | 5466-77-3 |
| 12 | 2-Hydroxy-4-methoxybenzophenone-5-sulfone (Sulisobenzonum) and the sodium salt | 4065-45-6 |
| 13 | 3-(4'-Sulfo)benzylidenebornan-2-one and salts | 58030-58-6 |
| 14 | 3-(4'-Methyl)benzylidenebornan-2-one | 36861-47-9 |
| 15 | 3-Benzylidenebornan-2-one | 16087-24-8 |
| 16 | 1-(4'-Isopropylphenyl)-3-phenylpropane-1,3-dione | 63260-25-9 |
| 17 | 4-Isopropylbenzyl salicylate | 94134-93-7 |
| 18 | 2,4,6-Trianiline(o-carbo-2'-ethylhexyl-1'-oxy)-1,3,5-triazine | 88122-99-0 |
| 19 | 3-4-Imidazolylacrylic acid and its ethyl ester | 104-98-3* |
| 20 | Ethyl 2-cyano-3,3-diphenylacrylate | 5232-99-5 |
| 21 | 2'-Ethylhexyl 2-cyano-3,3-diphenylacrylate | 6197-30-4 |
| 22 | Menthyl o-aminobenzoate or: 5-methyl-2-(1-methylethyl) 2-aminobenzoate | 134-09-8 |
| 23 | Glyceryl p-aminobenzoate or: 1-glycearyl 4-aminobenzoate | 136-44-7 |
| 24 | 2,2'-Dihydroxy-4-methoxybenzophenone (dioxybenzone) | 131-53-3 |
| 25 | 2-Hydroxy-4-methoxy-4-methylbenzophenone (mexonone) | 1641-17-4 |
| 26 | Triethanolamine salicylate | 2174-16-5 |
| 27 | Dimethoxyphenylglyoxalic acid or: Sodium 3,4-dimethoxyphenylglyoxalate | |
| 28 | 3-(4'Sulfo)benzylidenebornan-2-one and its salts | 56039-58-8 |

Mention should also finally be made of micronized pigments such as titanium dioxide and zinc oxide.

The compounds to be used according to the invention are, as a rule, distinguished by a particularly high absorbance in the UV-A radiation region. They are also readily soluble in cosmetic oils and can easily be incorporated into cosmetic formulations. The emulsions prepared with the compounds I are particularly distinguished by their high stability, the compounds I themselves by their high photostability, and the formulations prepared with I by their pleasant sensation on the skin.

U.S. Pat. No. 3,270,045 (1966) discloses the use of compounds of the formula

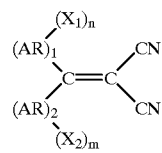

where AR is an aromatic radical and $X_1$ is also an alkoxy radical, as light stabilizers for organic materials which are altered by UV radiation, especially plastics. Among the large number of substances to be stabilized against UV radiation, such as plastic materials, sheets, foamed materials, whose surface is to be protected, also mentioned are "polishes, creams, lotions and the like". However, the skilled worker is unable to derive the teaching of the present invention from the complete context of this patent, ie. (a) to use these compounds as sunscreen agents for the human skin, (b) to make a selection in respect of UV-A absorbers and (c) to use these in combination with compounds which absorb in the UV-B region and are known per se for cosmetic formulations.

This is all the more true since this reference is from 1966 and, as explained at the outset, to date no stable UV-A absorbers have been available for cosmetic application; on the contrary, the development has been in the direction of external stabilization of UV-A absorbers which are unstable on their own.

PREPARATION

EXAMPLE 1

General method:

0.2 mol of alkylated benzophenone in 200 ml of heptane is mixed with an equimolar amount of malonitrile and 20 ml of a catalyst mixture consisting of amonium acetate/glacial acetic acid (molar ratio 1:4) and refluxed with a water trap for 20 h. Each hour during the reaction, a further 3 ml of the catalyst mixture are added. Subsequently the remaining catalyst is removed at about 50° C. and cooled to room temperature. The products precipitate. This is followed by filtration with suction and crystallization several times from ethyl acetate. Products which result as an oil are purified on a silica gel column with methylene chloride as eluent (yield: 35%). Table 1 shows the individual substances prepared.

TABLE 1

| Compound No. | Structure | λmax. [nm] (CH$_2$CL$_2$ [sic]) | $E_1^1$ | m.p. [° C.] |
|---|---|---|---|---|
| 1 | (structure with H$_{25}$C$_{12}$O) | 360 | 470 | 64–66 |
| 2 | (structure with H$_9$C$_4$O) | 360 | 630 | 80–82 |
| 3 | (structure with H$_7$C$_3$O groups) | 344 | 730 | 90–94 |
| 4 | (structure with H$_{17}$C$_8$O groups) | 346 | 460 | oil |

General method for producing emulsions for cosmetic purposes

All the oil-soluble ingredients are heated to 85° C. in a stirred vessel. When all the ingredients have melted and are present in the liquid phase, the aqueous phase is incorporated with homogenization. The emulsion is cooled to about 40° C. with stirring, is perfumed, homogenized and then cooled to 25° C. with continuous stirring.

FORMULATIONS

EXAMPLE 2

Composition for lip protection

| | |
|---|---|
| ad 100 | Eucerinum anhydricum |
| 10.00 | Glycerol |
| 10.00 | Titanium dioxide |
| 0.5–10 | Compound of Table 1, No. 2 |
| 8.00 | Octyl methoxycinnamate |
| 5.00 | Zinc oxide |
| 4.00 | Castor oil |
| 4.00 | Pentaerythrithil stearate/caprate/caprylate adipate |
| 3.00 | Glyceryl stearate SE |
| 2.00 | Beeswax |
| 2.00 | Microcrystalline wax |
| 2.00 | Quaternium-18 bentonite |
| 1.50 | PEG-45/dodecyl glycol copolymer |

EXAMPLE 3
Composition for sunblocker with micropigments

| | |
|---|---|
| ad 100 | Water |
| 10.00 | Octyl methoxcinnamate |
| 6.00 | PEG-7-hydrogenated castor oil |
| 6.00 | Titanium dioxide |
| 0.5–10 | Compound of Table 1, No. 4 |
| 5.00 | Mineral oil |
| 5.00 | Isoamyl p-methoxycinnamate |
| 5.00 | Propylene glycol |
| 3.00 | Jojoba oil |
| 3.00 | 4-Methylbenzylidene camphor |
| 2.00 | PEG-45/dodecyl glycol copolymer |
| 1.00 | Butyl methoxydibenzoylmethane |
| 1.00 | Dimethicone |
| 0.50 | PEG-40-hydrogenated castor oil |
| 0.50 | Tocopheryl acetate |
| 0.50 | Phenoxyethanol |
| 0.20 | EDTA |

EXAMPLE 4
Fat-free gel

| | |
|---|---|
| ad 100 | Water |
| 8.00 | Octyl methoxycinnamate |
| 7.00 | Titanium dioxide |
| 0.5–10 | Compound of Table 1, No. 2 |
| 5.00 | Glycerol |
| 5.00 | PEG-25 PABA |
| 1.00 | 4-Methylbenzylidene camphor |
| 0.40 | Acrylate C10—C30 alkyl acrylate crosspolymer |
| 0.30 | Imidazolidinyl urea |
| 0.25 | Hydroxyethyl cellulose |
| 0.25 | Sodium methylparaben |
| 0.20 | Disodium EDTA |
| 0.15 | Fragrance |
| 0.15 | Sodium propylparaben |
| 0.10 | Sodium hydroxide |

EXAMPLE 5
Sun cream (SPF 20)

| | |
|---|---|
| ad 100 | Water |
| 8.00 | Octyl methoxycinnamate |
| 8.00 | Titanium dioxide |
| 6.00 | PEG-7-hydrogenated castor oil |
| 0.5–10 | Compound of Table 1, No. 2. |
| 6.00 | Mineral oil |
| 5.00 | Zinc oxide |
| 5.00 | Isopropyl palmitate |
| 5.00 | Imidazolidinyl urea |
| 3.00 | Jojoba oil |
| 2.00 | PEG-45/dodecyl glycol copolymer |
| 1.00 | 4-Methylbenzylidene camphor |
| 0.60 | Magnesium stearate |
| 0.50 | Tocopheryl acetate |
| 0.25 | Methylparaben |
| 0.20 | Disodium EDTA |
| 0.15 | Propylparaben |

EXAMPLE 6
Sun cream water-resistant

| | |
|---|---|
| ad 100 | Water |
| 8.00 | Octyl methoxycinnamate |
| 5.00 | PEG-7-hydrogenated castor oil |
| 5.00 | Propylene glycol |
| 4.00 | Isopropyl palmitate |
| 4.00 | Caprylic/capric triglyceride |
| 0.5–10 | Compound in Table 1, No. 3 |
| 4.00 | Glycerol |
| 3.00 | Jojoba oil |
| 2.00 | 4-Methylbenzylidene camphor |
| 2.00 | Titanium dioxide |
| 1.50 | PEG-45/dodecyl glycol copolymer |
| 1.50 | Dimethicone |
| 0.70 | Magnesium sulfate |
| 0.50 | Magnesium stearate |
| 0.15 | Fragrance |

EXAMPLE 7
Sun milk (SPF 6)

| | |
|---|---|
| ad 100 | Water |
| 10.00 | Mineral oil |
| 6.00 | PEG-7-hydrogenated castor oil |
| 5.00 | Isopropyl palmitate |
| 3.50 | Octyl methoxycinnamate |
| 0.5–10 | Compound in Table 1, No. 2 |
| 3.00 | Caprylic/capric triglyceride |
| 3.00 | Jojoba oil |
| 2.00 | PEG-45/dodecyl glycol copolymer |
| 0.70 | Magnesium sulfate |
| 0.60 | Magnesium stearate |
| 0.50 | Tocopheryl acetate |
| 0.30 | Glycerol |
| 0.25 | Methylparaben |
| 0.15 | Propylparaben |
| 0.05 | Tocopherol |

We claim:

1. A sun-screen cosmetic formulation for protecting the human skin from the sun's rays which comprises: a cosmetically suitable carrier, at least one compound of the formula

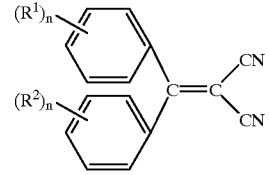

I where $R^1$ and $R^2$ are identical or different straight-chain or branched aliphatic or cycloaliphatic radicals which are in the para and/or ortho position and have 1 to 18 carbon atoms, and where $R^1$ may additionally be hydrogen atom, and where furthermore n is 1 or 2, as UV-A filters and at least one compound which absorbs the sun's rays in the UV-B region.

2. A cosmetic formulation as defined in claim 1, which contains at least one compound of the formula I wherein the aliphatic radicals in the position of $R^1$ and $R^2$ are identical or different straight-chain or branched alkyl radicals having 1 to 18 carbon atoms, in which the alkyl chain can be interrupted by oxygen atoms, and where $R^1$ can also be hydrogen.

3. A cosmetic formulation as defined in claim 1, wherein the aliphatic radicals in the position of $R^1$ and $R^2$ are identical or different branched alkoxy radicals which are in the para position and have 3 to 12 carbon atoms, and n is in each case 1, and $R^1$ can additionally be hydrogen.

4. A sunscreen-containing cosmetic formulation as defined in claim 1, wherein the cosmetically suitable carrier comprises at least one oil phase.

* * * * *